United States Patent [19]

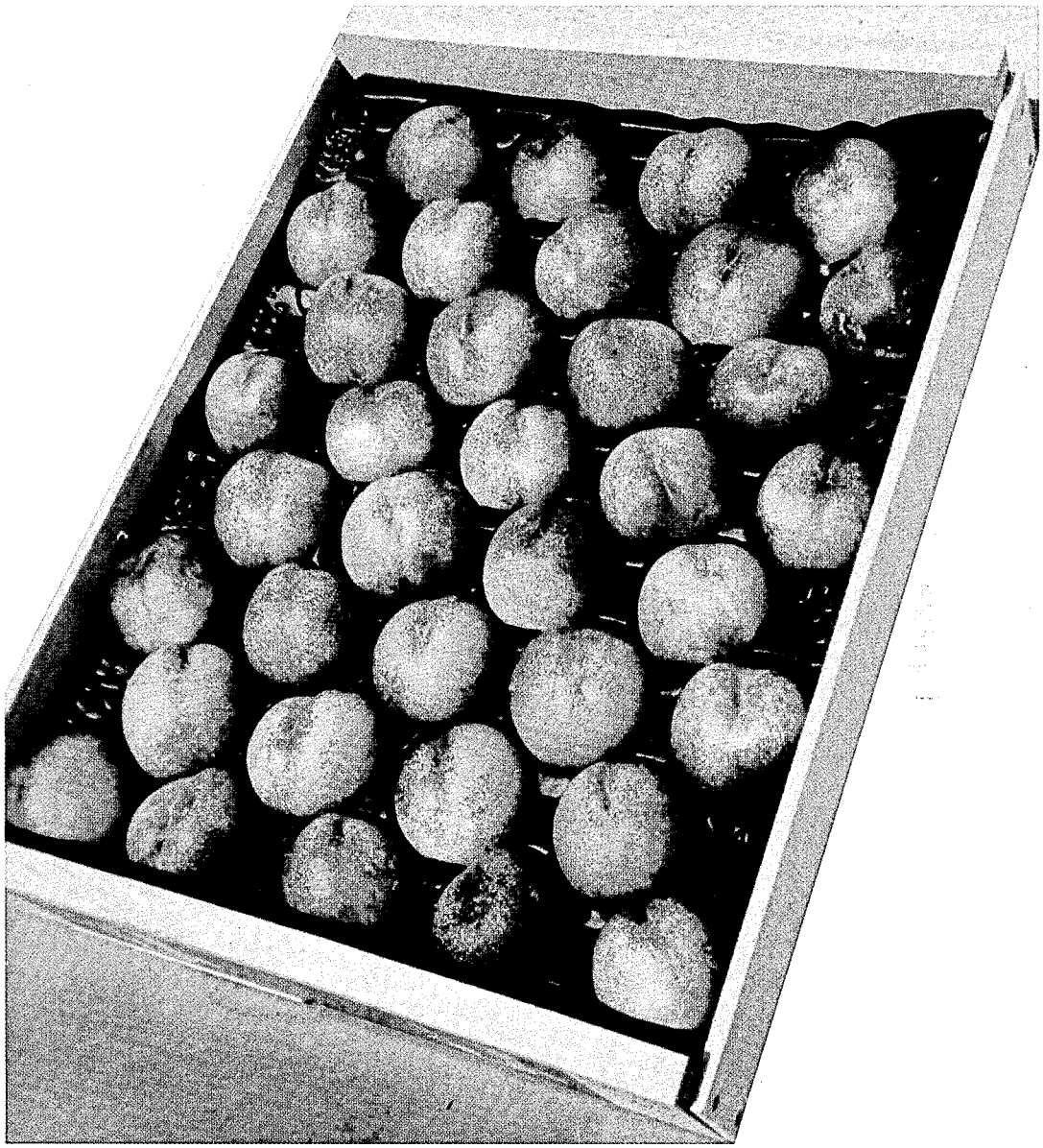

Kovacevich

[11] Plant 4,042

[45] Apr. 19, 1977

[54] NECTARINE TREE

[76] Inventor: John J. Kovacevich, P.O. Bin 488, Arvin, Calif. 93203

[21] Appl. No.: 690,972

[22] Filed: May 28, 1976

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Huebner & Worrel

[57] ABSTRACT

A nectarine tree generally similar to the Sunrise Nectarine Tree of U.S. Plant Pat. No. 1256 which bears yellow fleshed semi-freestone fruit from 10 days to 2 weeks earlier than the Sunrise.

1 Drawing Figure

BACKGROUND OF THE VARIETY

The present discovery relates to a new and distinct variety of nectarine tree which is generally similar in tree and fruit to the Sunrise Nectarine Tree of U.S. Plant Pat. No. 1,256, of which it is a sport, but which bears fruit which ripens from 10 days to 2 weeks earlier than the Sunrise, approximately at the same time as Armking of U.S. Plant Pat. No. 2,943 and 7 to 10 days after the Mayred of U.S. Plant Pat. No. 2,758.

The competition in fresh produce is perhaps most acute among fresh fruits. The market prices thereof are frequently known to vary several hundred percent over brief periods under the influence of supply and demand. Such wide fluctuations can cause the produce farmer the difference between a highly lucrative season or one in which he fails to recover his costs. Thus, the production of high quality fruit at a time when there is little or no competition is a major objective of most fresh fruit growers. In view of this, many fruit growers are continually on the alert for sports and mutations which produce high quality fruit earlier or later than similar fruit or superior fruit during the regular season. This continual quest resulted in the discovery and propagation of the subject variety.

ORIGIN AND ASEXUAL REPRODUCTION OF THE NEW VARIETY

My attention was initially attracted to the new variety growing in an orchard of Sunrise nectarine trees (U.S. Plant Pat. No. 1,256) on my farm near Wheeler Ridge, Kern County, Calif. by its production of fruit substantially identical to that of the Sunrise nectarine but ripening 10 days to 2 weeks earlier. The orchard had been an orchard of Mayred nectarine trees (U.S. Plant Pat. No. 2,758) which was grafted over to the Sunrise in 1965.

When I recognized this distinctive early ripening characteristic of the new variety, I undertook the asexual reproduction of it with the intent of perpetuating and commercializing such variety. This was first successfully accomplished by me by grafting the new variety into a Robin peach tree (U.S. Plant Pat. No. 529) on my farm near Wheeler Ridge. By careful observation of this and other grafts of the new variety onto other peach and nectarine trees, it has been determined that the grafted progeny consistently and reliably display the same characteristics as the original sport on the Sunrise tree, all as hereinafter more fully described.

SUMMARY OF THE NEW VARIETY

The instant variety of nectarine tree is characterized by perpetuating all of the general characteristics of the Sunrise nectarine except for its important distinction of ripening from 10 days to 2 weeks earlier under the growing conditions prevailing in the San Joaquin Valley of Calif. Its ripening period can also be characterized as being from 7 to 10 days later than the Mayred nectarine or with the Armking nectarine (U.S. Plant Pat. No. 2,943).

The new nectarine tree is of vigorous growth. It produces light pink blossoms fading from approximately "strong red", 2.5R 5/12 at their centers to a "pale pink", 2.5R 9/3, at their petal extremities. The fruit sets somewhat less abundantly than that of the Armking and is substantially spherical. The fruit is semi-freestone, has "brilliant yellow", 5Y 9/9, flesh, pale "yellowish brown", 7.5YR 5/7, stones and skin which is basically "brilliant yellow", 5Y 9/9, splashed with "dark red", 5R 3/7. The red frequently predominates.

BRIEF DESCRIPTION OF THE DRAWING

The drawing is a photographic reproduction in color of a box of nectarines of the subject variety, as packed for market.

DETAILED DESCRIPTION

The botanical details of the new and distinct variety of nectarine tree are as follows with color definitions by reference to the Nickerson Color Fan:

Tree:

*Size.*—Normal, similar to Sunrise under similar pruning and cultural conditions.

*Vigor.*—Vigorous.

*Figure.*—Upright, spreading.

*Productivity.*—Good but sets somewhat less than Armking.

*Regularity of bearing.*—Regular.

*Trunk.*—Stocky.

*Branches.*—Stocky. Size: Average. Surface character: Usual for nectarine trees. Color: "Moderate Olive" 2.5Y 4/4 to "Light Olive" 5Y 5/6. Lenticels: Number — Medium. Size — Medium.

*Leaves.*—Size: Normal for nectarine trees. Shape: Lanceolate. Color: "Moderate Olive Green" 7.5GY 4/4. Stem: "Brilliant Yellow Green" 5 GY 8/8. Marginal Form: Crenate. Glandular characteristics: Slightly reniform.

Flowers:

*Dates of bloom.*—Approximately with Sunrise.

*Size.*—Normal.

*Color.*—Generally light pink fading from "strong red", 2.5R 5/12, at center to "pale pink", 2.5R 9/3 at petal extremities.

Fruit:

*Maturity.*—10 days to 2 weeks earlier than Sunrise, 7 to 10 days after Mayred and approximately with Armking.

*Size.*—Uniformity: Uniform. Length: 5.7 to 6.1 cm. under normal cultural practices. Transverse in suture plane: 6.4 cm. Transverse at right angles to suture plane: 6.4 cm.

*Form.*—Uniformity: Uniform, globose. Symmetrical or asymmetric: Symmetrical. Suture: Shallow. Length: From stem to point. Ventril surface: Rounded. Stem cavity: Elongated in suture plane, medium depth. Base: Rounded and smooth. Pistil point: None. Stem: Length — 1.1 cm. Caliper — 0.31 cm. Skin: thickness — Thin but tough. Tendency to crack — None observed. Color — "Brilliant Yellow", 5Y 9/9, to "Dark Red", 5R 3/7, with the red frequently predominating. Pubescence — None.

*Flesh.*—Color: "Brilliant Yellow", 5Y 9/9. Surface of pit cavity: Normal ridges and grooves. Color of pit well: "Yellowish Brown", 10YR 5/6. Juice: Normal. Flavor: Excellent. Aroma: Present. Texture: Medium, firm and crisp to melting when fully ripe. Fibers: Minor. Ripening: Even. Eating quality: Excellent.

*Stone.*—Free or Cling: Semi-freestone. Fibers: Minor. Length: 3.5 cm. Width in suture plane: 2.8 cm. Width normal to suture plane: 1.9 cm. Form: Oblong to oval. Base: Flattened. Sides: Approximately uniform. Ridges: Medium width and depth. Color: Pale "yellowish brown", 7.5YR 5/7. Splitting tendency: None observed.

*Use.*—Principally fresh and frozen.

*Keeping quality.*—Excellent.

*Shipping quality.*—Excellent.

*Resistance to disease.*—None observed.

It is to be understood that normal variations in the described characteristics of the new variety nectarine tree result from environmental changes, such as in climate and soil conditions, and from changes in cultural practices, such as in pruning, thinning, fertilizing, spraying, irrigating and the like. The preceding description is that of the new variety produced under the ecological conditions prevailing at my farm near Wheeler Ridge, Calif. and the described characteristics are found to hold true in asexual reproduction of the variety.

What is claimed is:

1. A new and distinct variety of nectarine tree, substantially as illustrated and described, which is generally similar in tree and fruit to the Sunrise Nectarine Tree of U.S. Plant Pat. No. 1,256, of which it is a sport, but which bears fruit which ripens from 10 days to 2 weeks earlier than the Sunrise, approximately at the same time as the Armking of U.S. Plant Pat. No. 2,943 and 7 to 10 days after the Mayred of U.S. Plant Pat. No. 2,758.

* * * * *

UNITED STATES PATENT AND TRADEMARK OFFICE

CERTIFICATE OF CORRECTION

PATENT NO. : PP-4,042

DATED : April 19, 1977

INVENTOR(S) : John J. Kovacevich

It is certified that error appears in the above-identified patent and that said Letters Patent are hereby corrected as shown below:

Column 1, line 8, between "as" and "Armking"

insert --- the ---.

Signed and Sealed this

*fifth* Day of *July 1977*

[SEAL]

*Attest:*

RUTH C. MASON
*Attesting Officer*

C. MARSHALL DANN
*Commissioner of Patents and Trademarks*